(12) United States Patent
Wei

(10) Patent No.: US 11,313,855 B2
(45) Date of Patent: Apr. 26, 2022

(54) METHODS AND COMPOSITIONS FOR REMOVING BIOTIN INTERFERENCE FROM ASSAYS USING CONJUGATED MOLECULAR TRAPS

(71) Applicant: Siemens Healthcare Diagnostics Inc., Tarrytown, NY (US)

(72) Inventor: Tie Wei, Wilmington, DE (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 0 days.

(21) Appl. No.: 17/250,557

(22) PCT Filed: Sep. 19, 2019

(86) PCT No.: PCT/US2019/051887
§ 371 (c)(1),
(2) Date: Feb. 3, 2021

(87) PCT Pub. No.: WO2020/068547
PCT Pub. Date: Apr. 2, 2020

(65) Prior Publication Data
US 2021/0247388 A1 Aug. 12, 2021

Related U.S. Application Data

(60) Provisional application No. 62/735,913, filed on Sep. 25, 2018.

(51) Int. Cl.
*G01N 33/53* (2006.01)

(52) U.S. Cl.
CPC .................. *G01N 33/5306* (2013.01)

(58) Field of Classification Search
CPC .................................. G01N 33/5306
See application file for complete search history.

(56) References Cited

U.S. PATENT DOCUMENTS

| 5,212,063 A * | 5/1993 | Ofenloch-Hahnle ........................ G01N 33/538 435/7.5 |
|---|---|---|
| 5,929,049 A | 7/1999 | Singh et al. |
| 6,231,982 B1 | 5/2001 | Wang |
| 2006/0105372 A1 | 5/2006 | Craig et al. |
| 2006/0223126 A1 | 10/2006 | Tamori et al. |
| 2021/0311031 A1 * | 10/2021 | Wei .................... G01N 33/5306 |

FOREIGN PATENT DOCUMENTS

| EP | 2479268 | 7/2012 |
|---|---|---|
| JP | H02309254 | 12/1990 |
| JP | 2001513203 | 8/2001 |
| JP | 2006307126 | 11/2006 |
| JP | 2008307116 | 12/2008 |
| JP | 2010533872 | 10/2010 |
| WO | 2011051680 | 5/2011 |

OTHER PUBLICATIONS

George A. Orr. The Use of the 2-Iminobiotin-Avidin Interaction for the Selective Retrieval of Labeled Plasma Membrane Components. The Journal of Biological Chemistry 256 (2): 761-766 (Jan. 25, 1981).*
Freitag et al. Use of the Avidin (Imino)Biotin System as a General Approach to Affinity Precipitation. Methods in Molecular Biology 418: 35-50 (Feb. 2008).*
International Search Report for PCT/US2019/051887 dated Feb. 11, 2020.
Hofstetter, Heike et al: "A Labeling, Detection, and Purification System Based on 4-Hydroxyazobenzene-2-carboxylic Acid: An Extension of the Avidin-Biotin System"; Analytical Biochemistry, 284:2, pp. 354-366, (2000).
Morris, John E. et al: "Affinity Precipitation of Proteins by Polyligands"; Biotechnology and Bioengineering; vol. 41; pp. 991-997, (1993).

* cited by examiner

*Primary Examiner* — Gailene Gabel

(57) ABSTRACT

The present invention relates to methods and compositions to remove or reduce biotin interference from certain assays.

19 Claims, 3 Drawing Sheets

Specification includes a Sequence Listing.

SEQUENCE LISTING

```
<160> NUMBER OF SEQ ID NOS: 2

<210> SEQ ID NO 1
<211> LENGTH: 128
<212> TYPE: PRT
<213> ORGANISM: Gallus gallus
```

```
<400> SEQUENCE: 1

Ala Arg Lys Cys Ser Leu Thr Gly Lys Trp Thr Asn Asp Leu Gly Ser
1               5                   10                  15

Asn Met Thr Ile Gly Ala Val Asn Ser Arg Gly Glu Phe Thr Gly Thr
            20                  25                  30

Tyr Thr Thr Ala Val Thr Ala Thr Ser Asn Glu Ile Lys Glu Ser Pro
        35                  40                  45

Leu His Gly Thr Glu Asn Thr Ile Asn Lys Arg Thr Gln Pro Thr Phe
    50                  55                  60

Gly Phe Thr Val Asn Trp Lys Phe Ser Glu Ser Thr Thr Val Phe Thr
65                  70                  75                  80

Gly Gln Cys Phe Ile Asp Arg Asn Gly Lys Glu Val Leu Lys Thr Met
            85                  90                  95

Trp Leu Leu Arg Ser Ser Val Asn Asp Ile Gly Asp Asp Trp Lys Ala
            100                 105                 110

Thr Arg Val Gly Ile Asn Ile Phe Thr Arg Leu Arg Thr Gln Lys Glu
            115                 120                 125

<210> SEQ ID NO 2
<211> LENGTH: 127
<212> TYPE: PRT
<213> ORGANISM: Streptomyces avidinii

<400> SEQUENCE: 2

Ala Ala Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
            85                  90                  95

Trp Leu Leu Thr Ser Gly Thr Thr Glu Ala Asn Ala Trp Lys Ser Thr
            100                 105                 110

Leu Val Gly His Asp Thr Phe Thr Lys Val Lys Pro Ser Ala Ala
            115                 120                 125
```

METHODS AND COMPOSITIONS FOR REMOVING BIOTIN INTERFERENCE FROM ASSAYS USING CONJUGATED MOLECULAR TRAPS

The subject application claims benefit under 35 USC § 119(e) of U.S. provisional Application No. 62/735,913, filed Sep. 25, 2018. The entire contents of the above-referenced patent application are hereby expressly incorporated herein by reference.

FIELD OF THE INVENTION

The present invention relates to methods and compositions for assays and for removing interference, particularly biotin interference from such assays.

BACKGROUND OF THE INVENTION

In modern in-vitro clinical diagnostics, a variety of methods are utilized for the detection of analytes in a sample. In one form of a diagnostic method, an immunoassay, one or more specifically binding species are used. Typical examples are the sandwich immunoassay, where two specifically binding species (antibody or antigen) bind to the analyte of interest, and the competitive immunoassay, where the analyte of interest and an analog of this analyte compete for binding to a specifically binding species. In a competitive immunoassay, the antigen is also often referred to as a hapten or ligand. One of the specifically binding species is commonly attached to a so-called label or tag, which may be an atom (e.g., radioactive), molecule (e.g., an enzyme, fluorescent, or luminescent compound) or particle (magnetic or latex). This label allows for detection of the analyte of interest through a variety of detection methods corresponding to the label utilized. In a competitive assay, either the specifically binding species or the analyte analog can carry the label. The other specifically binding species is frequently associated to a solid or suspendable substrate ("the solid phase") covalently or through adsorption. Alternatively, the specifically binding species may be linked to a first member of a second binding pair (e.g., biotin), while the second member of the second binding pair (e.g., streptavidin) is attached to the solid phase. This allows the specifically binding species to bind to the solid phase via the second binding pair interaction (e.g., biotin-streptavidin).

Haptens such as biotin and fluorescein are often used to conjugate with antibodies or other small drug molecules in assay reagents. Their tight binding to large protein molecules (e.g., streptavidin to biotin and anti-FITC antibody to fluorescein) coated on solid support provides a convenient way to immobilize hapten-Ab or hapten-drug on the solid surface. Since the binding force between biotin and streptavidin or avidin displays one of the highest constants for biological molecules, biotin is very frequently used as ligand and streptavidin as specific binding partner therefor.

It is important for the stability and reproducibility of the diagnostic assay that the binding ability of the solid-phase bound species for its binding partner does not become impaired over time. This may result in decreased reliability and decreased assay sensitivity. One mechanism that may lead to such impairment (apparent as instability) is bleeding of a portion of the solid-phase-attached species into the surrounding medium. The free species competes with the solid-phase-attached species for binding to the target and usually has a significant kinetic advantage due to its faster diffusion. Therefore, it is advantageous to maintain the amount of free species competing with the solid phase-attached species in a reagent constant, preferably very close to zero. This would allow for the sensitive detection of analytes in a stable and reproducible manner. The preferred way of eliminating free species is to find a binding method that will eliminate dissociation. Covalent bonding, as opposed to adsorptive association, might be the method of choice, due to its greater bond strength. However, in many cases this may be impossible or impractical, for various reasons.

Biotin has found use as a supplement. Biotin as a food supplement, for example, is aimed to promote healthy hair and nail growth and treat other disease conditions. Thus, the quantities of biotin in serum may be quite high. Because molecules such as biotin are used in many diagnostic assays to coat solid support, bind to antibodies or hapten analogs, these high levels of biotin in blood may interfere with the assay signal. Therefore, if biotin is present in the sample solutions in free form, it occupies binding sites and can, therefore, lead to false results of the test. This is especially critical in the case of patients who received highly dosed amounts of biotin. It is assumed that biotin in an amount of more than 30 ng/ml of sample already results in falsified results. In the case of patients treated with biotin, serum values of up to 180 ng/ml or even up to 1500 ng/ml and long-lasting values of about 70 ng/ml can occur.

One method to mitigate such interference relates to the use of preformed reagent, that is, pre-bound biotinylated assay component with the streptavidin coated solid support during reagent production. Because of the tight bound and slow off-rate between streptavidin and biotin, replacing the already bound biotin from streptavidin by the incoming biotin in patient sample is not a predominating process.

The second way is to increase the streptavidin binding sites on the solid support, so that there are extra binding sites available for the sample biotin molecules in addition to the biotinylated assay components. The third way is the combination of both of the above. But none of the above truly solves the biotin interference issue unless we totally stay away from using biotin-streptavidin as active assay components.

One major issue with all the above solutions is that assay components are involved in the interference prevention, which may easily affect the magnitude of the assay signal itself. Assays components used in such cases get away from optimum conditions to detect intended analytes. Some examples are provided in U.S. Pat. No. 8,252,605.

Another method is disclosed in U.S. Pat. No. 5,212,063. It discloses the use of polymer particles with a biotin binding core and a covering layer of protein, carbohydrate or co-polymer to filter through free biotin but not biotin-conjugated to large molecules.

This approach may be effective for some assay format but the introduction of particles may generate extra-absorbance that could interference with assay signals.

Therefore, it is an object of the present invention to provide improved processes for the mitigation of such substances in assays so that the detection process is not disturbed. Therefore, a method is required to remove the biotin so that a disturbance of the test does not take place.

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

The terms "analog" and "derivative" are used herein interchangeably and refer to a substance which comprises the same basic carbon skeleton and carbon functionality in its structure as a given compound, but can also contain one or more substitutions thereto. The term "substitution" as used herein will be understood to refer to the replacement of at least one substituent on a compound with a residue R. In certain non-limiting embodiments, R may include H, hydroxyl, thiol, a halogenide selected from fluoride, chloride bromide or iodine, a C1-C4 compound selected one of the following: linear, branched or cyclic alkyl, optionally substituted, and linear branched or cyclic alkenyl, wherein the optional substituents are selected from one or more alkenylalkyl, alkynylalkyl, cycloalkyl, cycloalkenylalkyl, arylalkyl, heteroarylalkyl, heterocycloalkyl, optionally substituted heterocycloalkenylalkyl, arylcycloalkyl, and arylheterocycloalkyl, each of which is optionally substituted wherein the optional substituents are selected from one or more of alkenylalkyl, alkynylalkyl, cycloalkyl, cycloalkenylalkyl, arylalkyl, alkylaryl, heteroarylalkyl, heterocycloalkyl, optionally substituted heterocycloalkenylalkyl, arylcycloalkyl, and arylheterocycloalkyl, phenyl, cyano, hydroxyl, alkyl, aryl, cycloalkyl, cyano, alkoxy, alkylthio, amino, —NH (alkyl), —NH(cycloalkyl)$_2$, carboxy, and —C(O))-alkyl.

The term "sample" as used herein will be understood to include any type of biological sample that may be utilized in accordance with the present disclosure. Examples of fluidic biological samples that may be utilized include, but are not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "specific binding partner," or "sbp" as used in particular (but not by way of limitation) herein in the terms "biotin-specific binding partner" or "target analyte-specific binding partner," will be understood to refer to any molecule capable of specifically associating with biotin or the target analyte, respectively. For example but not by way of limitation, the binding partner may be an antibody, a receptor, a ligand, aptamers, molecular imprinted polymers (i.e., inorganic matrices), combinations or derivatives thereof, as well as any other molecules capable of specific binding to biotin or the target analyte, respectively.

The term "antibody" is used herein in the broadest sense and refers to, for example, intact monoclonal antibodies and polyclonal antibodies, multi-specific antibodies (e.g., bispecific antibodies), antibody fragments and conjugates thereof that exhibit the desired biological activity of analyte binding (such as, but not limited to, Fab, Fab', $F(ab')_2$, Fv, scFv, Fd, diabodies, single-chain antibodies, and other antibody fragments and conjugates thereof that retain at least a portion of the variable region of an intact antibody), antibody substitute proteins or peptides (i.e., engineered binding proteins/peptides), and combinations or derivatives thereof. The antibody can be of any type or class (e.g., IgG, IgE, IgM, IgD, and IgA) or sub-class (e.g., IgG1, IgG2, IgG3, IgG4, IgA1, and IgA2).

The term "hapten" as used herein refers to a small proteinaceous or non-protein antigenic determinant (or "epitope") which is capable of being recognized by a target analyte-specific binding partner, such as (but not limited to) an antibody. The term "polyhapten" as used herein will be understood to refer to a synthetic molecule that contains multiple epitopes/antigenic determinants attached thereto.

An "analyte" is a macromolecule that is capable of being recognized by an analyte-specific binding partner, such as (but not limited to) an antibody. Both analytes and haptens comprise at least one antigenic determinant or "epitope," which is the region of the antigen or hapten which binds to the analyte-specific binding partner (i.e., antibody). Typically, the epitope on a hapten is the entire molecule.

DETAILED DESCRIPTION

In one embodiment a hapten trap is added in the reagent formulation to remove the interfering hapten without the involvement of the assay components that generate assay signal.

The hapten trap may be a soluble or solid cage. If the trap has pores it should have pore sizes that only allow free biotin to enter the pores, but not allow large molecules such as the biotin-antibody to enter. Alternatively, or in addition the trap can be charged so that the haptens are drawn to the cage. The interior of the cage should be able to trap the interfering hapten molecules (biotin or fluorescein) either by hydrogen binding, hydrophobic interactions or molecular imprint, such as specific binding partners.

The molecular cages thus trap interfering hapten molecules, but not hapten-Ab conjugate to effectively reduce the hapten's accessibility to their binding partners in assay components.

Figure 1:
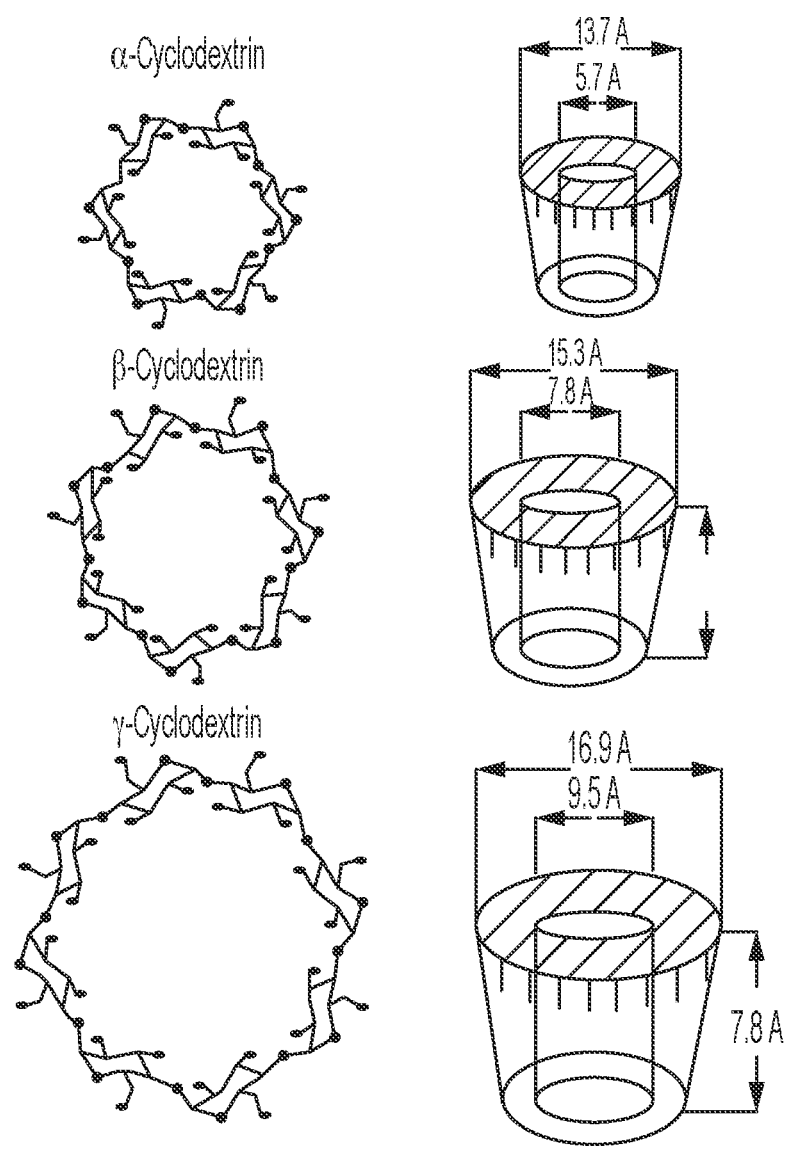
FIG. 1 schematically depicts various cyclodextrin traps.
Figure 2:
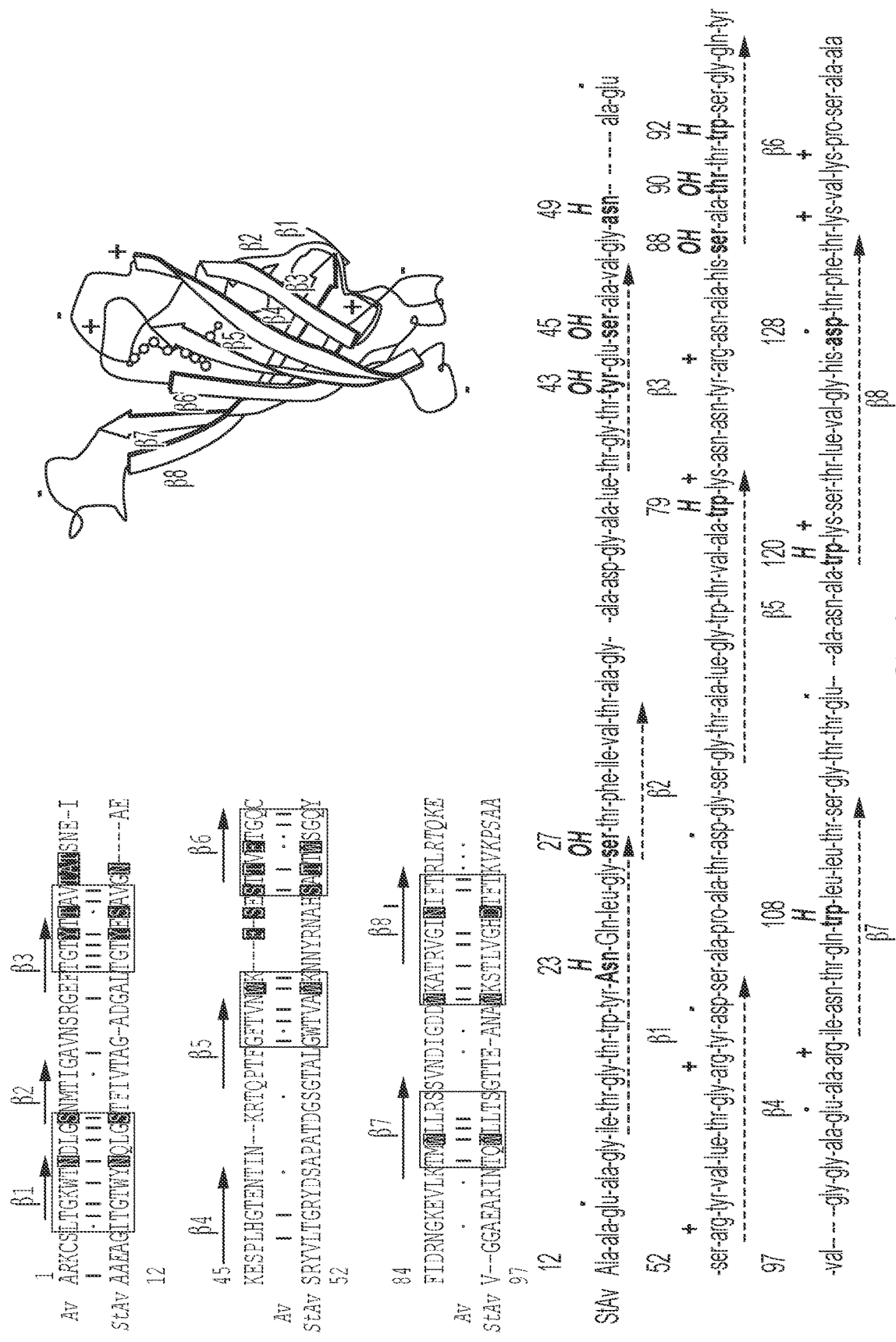
FIG. 2 schematically depicts amino acid structures of avidin and streptavidin.
Figure 3:
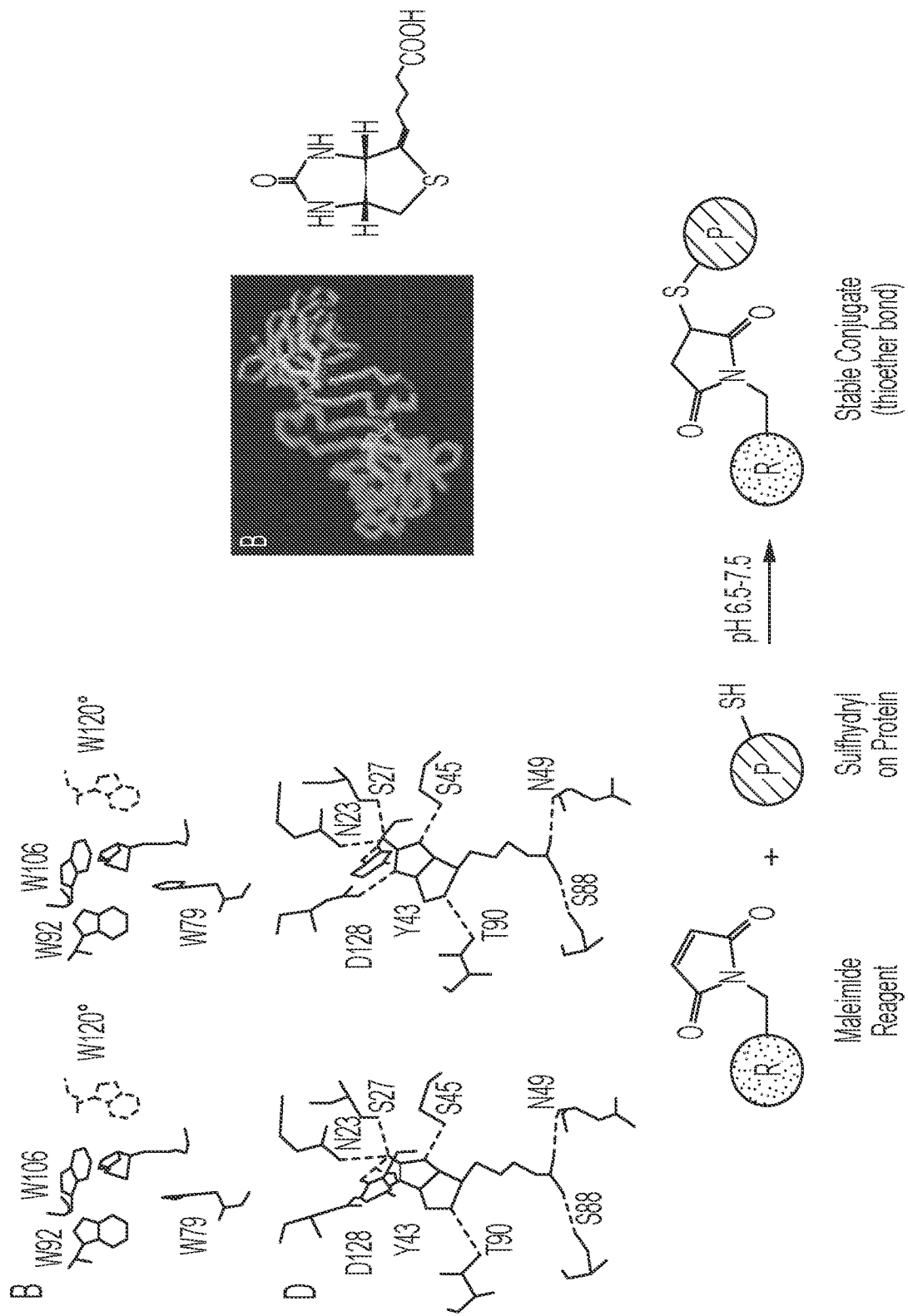
FIG. 3 schematically depicts maleimide chemistry for possible mutations.

Examples of molecular cages are cyclodextrins. The cyclodextrin may be chemically modified to better exclude hapten-conjugates. Other examples may involve synthesizing solid (buoyant) support or soluble complexes with inner-surface coated with aptamers, avidin, streptavidin or anti-FITC antibodies solid support (buoyant) or soluble complexes. This solid support or complexes should have molecular size exclusion small enough that allows only the target hapten to enter the cage but not large biotinylated antibodies. See FIG. 1.

Accordingly, the invention is a molecular trap to reduce free-hapten interference in an assay, the molecular trap comprising:
a molecular cage that comprises a shell that surrounds a cavity having characteristics to selectively capture and retain a hapten that is unconjugated or free in an assay solution. The shell of the molecular cage may be selected from the group consisting of a cyclodextrin shell and a molecular-imprint-specific binding partner shell for the hapten. In a particular embodiment the characteristics of the shell may have a selective permeability to the free-hapten or be a selective deterrent for the relatively larger assay components, such as an assay conjugate of the happen, or the shell may be a combination of both characteristics.

In some embodiments the molecular cage further comprises a coating on the shell, the coating being selectively permeable to the free-hapten and impermeable to relatively larger assay components present in the assay solution. The relatively larger assay components may include an assay-conjugate of the hapten, an assay specific binding partner (sbp) for the hapten, an assay-conjugate of the sbp, and other assay molecules of greater than about 1000 Daltons molecular weight or more preferably greater than about 2000 Dalton molecular weight. In some embodiments the coating comprises one or more of bovine serum albumin, dextran aldehyde, amino dextran, and an ionically charged moiety.

In some embodiments the cavity characteristics of the molecular cage comprises one or both of moieties with selective interaction with the free-hapten and a cavity size dimension conducive to selectively receive and retain the free-hapten and to preferentially exclude assay molecules greater than about 1000 Daltons molecular weight present in the assay solution or more preferably greater than about 2000 Daltons molecular weight. The cavity may comprise internal specific-binding moieties to selectively retain the received free-hapten. The cavity characteristics may comprise one or both of a cavity opening limited in size to selectively receive the free-hapten and to preferentially exclude assay molecules greater than about 1000 Daltons molecular weight present in the assay solution and an internal cavity interaction with the free-hapten comprising one or more of hydrogen-bonding, van der Waal forces, polar bonding, hydrophilic interaction, hydrophobic interaction, ionic attraction, lock-and-key interaction.

Typically the free-hapten in the assay solution is about one-tenth of a molecular weight of assay-conjugates of the hapten present in the assay solution, the cavity characteristics of the molecular cage comprising a cavity opening with a molecular weight exclusion limit at greater than the molecular weight of the free-hapten, and an internal cavity moiety with selective interaction with the free-hapten.

The shell may be a cyclodextrin shell with the cyclodextrin selected from the group consisting of alpha-cyclodextrin, beta-cyclodextrin and gamma-cyclodextrin.

The free-hapten may be selected from the group consisting of free-biotin and free-fluorescein. The specific binding partner to biotin of the molecular-imprint-specific binding partner shell may comprise one or more of streptavidin, avidin and traptavidin. If the free-hapten is free-fluorescein, the specific binding partner to fluorescein of the molecular-imprint-specific binding partner shell comprises anti-fluorescein antibody.

In another embodiment the hapten trap is added in the reagent formulation to minimize the interfering hapten from its binding partner without the involvement of the assay components that generate assay signal and without generating extra absorbance that may interference with true assay signal.

The trap may have the following features:
a) It is not a particle or solid phase agent but soluble molecular structures in aqueous solution.
b) It should only bind to free hapten but not to large molecules such as hapten-Ab conjugates.
Features described in a) and b) are sufficient to constitute a molecular hapten trap. Alternatively the following features are also deemed sufficient for the molecular hapten trap:
c) It has a slower off-rate for binding so that the bound hapten is practically locked in place. The advantage of this feature is that the trapped (or locked-in biotin) will not easily dissociate and compete with conjugated hapten for the assay signal generating hapten binding partner.
d) It should have a slower on-rate for binding so that the conjugated hapten will preferentially bind to assay signal generating hapten binding partner.
Molecular Hapten traps can sufficiently work with either features a) and b) or with features c) and d) alone or in combination.

Taking biotin-avidin (or streptavidin) as example, avidin or streptavidin can be chemically decorated with dexal or other spacer molecules via covalent bounds to form a surface layer that is only permeable to free biotin, but not to biotin moiety of the biotinylated antibody. Traptavidin is such a molecule that has 1/2 the on-rate and 1/10 the off-rate for biotin binding, making it a good biotin trap by pre-incubating with the biotin containing sample. One proposed assay example for LOCI PCT assay is as follows:
1) Incubate biotin containing sample with capture Ab coated chemibeads reagent that contains a soluble molecular biotin trap (for example, dexal-decorated streptavidin or traptavidin or un-decorated traptavidin). Free biotin in the sample will bind to the biotin trap.
2) Add biotinylated antibodies followed by streptavidin coated sensibeads. If native (un-decorated) traptavidin is used in step 1), streptavidin coated sensibeads will need to be added soon after the addition of biotinylated antibodies. This is to make sure biotinylated antibody preferentially bind to streptavidin coated on the sensibeads, not to traptavidin which has a slower on rate than streptavidin for biotin binding. If surface-decorated traptavidin that doesn't bind to conjugated biotin is used, the bound free biotin molecules from sample will not compete with biotinylated antibody for binding to streptavidin-sensibeads because they are locked in traptavidin molecules.

The field of medical diagnostics utilizes many different forms of assay technologies. One example of a commercially used assay is the Luminescent Oxygen Channeling Assay (LOCI®) technology. The LOCI® advanced chemiluminescence assay is described, for example, in U.S. Pat. No. 5,340,716 (Ullman et al.), the entire contents of which are expressly incorporated herein by reference. The currently available LOCI® technology has high sensitivity and uses several reagents. In particular, the LOCI® assay requires that two of these reagents (referred to as a "sensibead" and a "chemibead") be held by other specific binding partner assay reagents in a manner whereby the sensibead and chemibead are in close proximity to one another to achieve a signal. Upon exposure to light at a certain wavelength, the sensibead releases singlet oxygen, and if the two beads are in close proximity, the singlet oxygen is transferred to the chemibead; this causes a chemical reaction that results in the chemibead giving off light that can be measured at a different wavelength.

Particular, non-limiting examples of chemiluminescent compounds and photosensitizers that may be utilized in accordance with the present disclosure are set forth in U.S. Pat. No. 5,340,716 (Ullman, et al.), the entire contents of which are hereby expressly incorporated herein by reference.

Accordingly, the invention comprises a molecular trap to reduce free-hapten interference in an assay, the molecular trap comprising:

a molecular structure soluble in an assay solution to selectively bind free-hapten, the molecular structure comprising a modified specific binding partner (sbp) to the free-hapten. The modified sbp comprises one or more of a dextran aldehyde component, a bound steric-hindering polymer, and slower specific free-hapten binding off-rate characteristics than other free-hapten specific binding partners (sbps) assay reagents.

Such molecular structure may further comprise a coating, the coating comprising one or more of a selectively permeable material for the free-hapten, an ionic charge to one or both of attract the free-hapten and repel other assay molecules in the assay solution, and a polarity to facilitate one or both of selective retention of the free-hapten and steric repellence of the other assay molecules in the assay solution.

The coating may comprise one or more of proteins or peptides such as bovine serum albumin, polymers such as dextran aldehyde or amino dextran, compounds such as ethylenediamine, tetra-ethylene penta-amine, an ionically charged moiety, hydrophobic moiety (sulfo-N-hydroxy succinimide acetate) etc. The specific free-hapten binding off-rate characteristic of the modified sbp is slower than the specific free-hapten binding on-rate characteristic of the modified sbp.

In some embodiments the free-hapten is free-biotin, the modified sbp is traptavidin having the slower specific free-hapten binding off-rate than other free-hapten sbps in the assay solution, the other free-hapten sbps in the assay solution being selected from streptavidin and avidin.

The modified sbp may comprise one or both of a dextran aldehyde component and a steric-hindering polymer that selectively impede binding with assay components and assay-conjugates in the assay solution and that are relatively larger than the free-hapten.

In some embodiments, the free-hapten in the assay solution is selected from the group consisting of free-biotin and free-fluorescein, wherein the modified sbp to free-biotin is one of a modified streptavidin, a modified avidin, and a traptavidin and wherein the modified sbp to free-fluorescein is a modified anti-fluorescein.

The modified sbp may be a genetically engineered sbp comprising the steric-hindering polymer conjugated to an amino acid of the modified sbp adjacent to a specific binding site for the free-hapten, the steric-hindering polymer hinders specific binding of hapten-assay conjugates corresponding to the free-hapten.

The steric-hindering polymer is selected from the group consisting of amino dextran and bovine serum albumin.

The hapten-assay conjugates are selected from a group consisting of one or more of hapten-antibody conjugates, hapten-antigen conjugates, hapten-labeling enzyme conjugates, hapten-analyte-under-test conjugates, hapten-label conjugates, and hapten-receptor conjugates.

Creating hapten trap at the molecular level that is soluble in aqueous reaction mixture should allow much wider applications than hapten trap particles. The biotin lock-in mechanism given by traptavidin-like molecules greatly reduces the chance for free biotin to dissociate from the hapten trap and compete for sensibeads binding with biotinylated antibodies. Third is that slower binding to traptavidin allows biotinylated antibodies preferentially bind to the sensibeads in case native (un-decorated) traptavidin is used.

In yet another embodiment the hapten trap is a genetically engineered hapten binding protein (free hapten trap). The genetically engineered hapten trap is added in the reagent formulation to take away the interfering free hapten from its binding partner without the involvement of the assay components that generate assay signal and without generating extra absorbance that may interference with assay signal. Preparing the hapten trap involves the following:

a) site directed mutagenesis changes an amino-acid residue(s) near the biotin binding site, allowing conjugation of another protein or polymer near the binding site to provide steric hindrance for large biotinylated antibody but not smaller free hapten to enter the binding sites b) other genetic engineering techniques produce similar mutation as a)

c) Genetically engineered streptavidin still binds to free biotin with high affinity.

d) Conjugate a protein (such BSA) or polymer to the engineered streptavidin to complete the making of the free biotin trap.

e) Genetically engineered by site directed mutagenesis change one amino-acid residue to a unique amino-acid that is not in the current sequence. For example, change an amino acid residue on the connection sections between {37-{37, {35-{36, or {33-{34 (see FIG. 2) to Methionine (Met or M). Because the mutation is near the binding site, conjugating a protein using SMCC (maleimide chemistry) and/or other polymers will provide steric hindrance for biotinylated antibody reagent (see FIG. 3).

Accordingly, the invention comprises a molecular trap to reduce free-hapten interference in an assay, the molecular trap comprising a molecular complex soluble in an assay solution to selectively provide free-hapten competitive specific binding in the molecular complex. The molecular complex comprises a conjugate that comprises a hapten-analog, a steric-hindering polymer that is relatively larger than the hapten-analog, and a linking group to provide a flexible linker connection between the hapten-analog and the steric-hindering polymer; and, in addition an anti-hapten specific binding partner (sbp) interconnected with the conjugate. The hapten-analog having weaker specific binding characteristics to the anti-hapten sbp than free-hapten, the flexible linker connection providing a degree of freedom between the hapten-analog and a specific binding site on the anti-hapten sbp for hapten, the steric-hindering polymer preventing hapten-assay conjugates in the assay solution from accessing the specific binding site.

In the above molecular trap, the hapten may be biotin, the hapten-analog is selected from the group of 4'-hydroxyazobenzene-2-carboxylic acid (HABA) and 2-imino biotin, and the anti-hapten sbp being selected from streptavidin, avidin and traptavidin.

The weaker specific binding characteristics of the hapten-analog relative to the free-hapten may comprise a pH-dependent specific binding. The steric-hindering polymer of the molecular trap may be selected from proteins or peptides such as bovine serum albumin, polymers such as dextran aldehyde or amino dextran, compounds such as ethylenediamine, tetra-ethylene penta-amine, an ionically charged moiety, or hydrophobic moieties such as sulfo-N-hydroxy succinimide acetate.

The present invention includes a method of reducing interference by free-hapten in an assay, the method comprising:

combining assay components and a patient sample having an analyte-under-test and excess free-hapten to form an assay solution, the assay components comprising a specific binding pair including a hapten and a relatively larger anti-hapten, assay-conjugates of each of the hapten and the anti-hapten, and a molecular trap selective for the free-hapten; and selectively retaining the free-hapten in the assay solution with the molecular trap, wherein the molecular trap comprises one or a mixture of a molecular cage having a shell surrounding a cavity, a molecular complex, and a molecular structure comprising a modified anti-hapten specific binding partner (sbp), the modified anti-hapten sbp comprising one or more of a dextran aldehyde component, a bound steric-hindering polymer, and specific free-hapten binding off-rate characteristics that are slower than other anti-hapten specific binding partners (sbps) assay components.

In such method the specific free-hapten binding off-rate characteristic of the modified anti-hapten sbp is slower than the specific free-hapten binding on-rate characteristic of the modified anti-hapten sbp.

Further in such method, the molecular complex may be a hapten-analog conjugated with a steric-hindering polymer using a flexible linker and an anti-hapten sbp interconnected with the hapten-analog conjugate, the hapten-analog having same or weaker specific binding characteristics than the free-hapten to the anti-hapten sbp, the steric-hindering polymer preventing hapten-assay conjugates in the assay solution from accessing a specific hapten binding site on the anti-hapten sbp, and wherein the free-hapten in the assay solution preferably binds to the anti-hapten sbp specific binding site.

In such methods, the assay-conjugates of the hapten and the assay-conjugates of the anti-hapten are individually selected from the group of assay components consisting of an antibody, an antigen, an analyte-under-test, a label, a labeling enzyme, a receptor and a combination of two or more of the group.

What is claimed is:

1. A hapten trap to reduce free-hapten interference in an assay for a target analyte in a patient sample, the hapten trap comprising:
   a soluble molecular complex that is soluble in an assay solution to selectively provide free-hapten competitive specific binding in the molecular complex, the molecular complex comprising:
   a conjugate that comprises a hapten-analog, a steric-hindering polymer that is relatively larger than the hapten-analog, and a linking group to provide a flexible linker connection between the hapten-analog and the steric-hindering polymer; and
   an anti-hapten specific binding partner (sbp) interconnected with the conjugate, the hapten-analog having weaker specific binding characteristics to the anti-hapten sbp than free-hapten, the flexible linker connection providing a degree of freedom between the hapten-analog and a specific binding site on the anti-hapten sbp for hapten, the steric-hindering polymer preventing hapten-assay conjugates in the assay solution involved in the assay for the target analyte from accessing the specific binding site on the anti-hapten sbp for hapten; and
   wherein the hapten trap is not an assay component involved in generation of an assay signal for the target analyte.

2. The hapten trap of claim 1, wherein the hapten is biotin, the hapten-analog is selected from the group consisting of 4'-hydroxyazobenzene-2-carboxylic acid (HABA) and 2-imino biotin, and the anti-hapten sbp is selected from the group consisting of streptavidin, avidin, and traptavidin.

3. The hapten trap of claim 1, wherein the weaker specific binding characteristics of the hapten-analog relative to the free-hapten comprise a pH-dependent specific binding.

4. The hapten trap of claim 1, wherein the steric-hindering polymer is selected from the group consisting of bovine serum albumin, dextran aldehyde, amino dextran, ethylenediamine, tetra-ethylene penta-amine, an ionically charged moiety, or sulfo-N-hydroxy succinimide acetate.

5. The hapten trap of claim 1, wherein the hapten is fluorescein, and the anti-hapten specific binding partner is an anti-fluorescein antibody.

6. A kit for reducing free-hapten interference in an assay for a target analyte in a patient sample, comprising:
  at least two assay components for detection of a target analyte in a patient sample, wherein at least one of the at least two assay components contains an analyte-specific binding partner, and wherein a first assay component comprises a hapten-assay conjugate and a second assay component comprises an anti-hapten specific binding partner (sbp); and
  a hapten trap configured to reduce free-hapten interference in the assay for detection of the target analyte, the hapten trap comprising:
    a soluble molecular complex that is soluble in an assay solution to selectively provide free-hapten competitive specific binding in the molecular complex, the molecular complex comprising:
      a conjugate that comprises a hapten-analog, a steric-hindering polymer that is relatively larger than the hapten-analog, and a linking group to provide a flexible linker connection between the hapten-analog and the steric-hindering polymer; and
      an anti-hapten specific binding partner (sbp) interconnected with the conjugate, the hapten-analog having weaker specific binding characteristics to the anti-hapten sbp than free-hapten, the flexible linker connection providing a degree of freedom between the hapten-analog and a specific binding site on the anti-hapten sbp for hapten, the steric-hindering polymer preventing the hapten-assay conjugates in the assay solution involved in the assay for the target analyte from accessing the specific binding site on the anti-hapten sbp for hapten; and
    wherein the hapten trap is not an assay component involved in generation of an assay signal for the target analyte.

7. The kit of claim 6, wherein the hapten is biotin, the hapten-analog of the hapten trap is selected from the group consisting of 4'-hydroxyazobenzene-2-carboxylic acid (HABA) and 2-imino biotin, and the anti-hapten sbp of the hapten trap is selected from the group consisting of streptavidin, avidin, and traptavidin.

8. The kit of claim 6, wherein the weaker specific binding characteristics of the hapten-analog of the hapten trap relative to the free-hapten comprise a pH-dependent specific binding.

9. The kit of claim 6, wherein the steric-hindering polymer of the hapten trap is selected from the group consisting of bovine serum albumin, dextran aldehyde, amino dextran, ethylenediamine, tetra-ethylene penta-amine, an ionically charged moiety, or sulfo-N-hydroxy succinimide acetate.

10. The kit of claim 6, wherein the hapten is fluorescein, and the anti-hapten specific binding partner of the hapten trap is an anti-fluorescein antibody.

11. The kit of claim 6, wherein the hapten conjugate of the first assay component is selected from the group consisting of a hapten-antibody conjugate, a hapten-antigen conjugate, a hapten-labeling enzyme conjugate, a hapten-analyte-under-test conjugate, a hapten-label conjugate, and a hapten-receptor conjugate.

12. The kit of claim 6, wherein the hapten conjugate of the first assay component has a molecular weight of greater than about 1000 Daltons.

13. The kit of claim 6, wherein the first assay component comprises a biotinylated analyte-specific binding partner, and the second assay component comprises a streptavidin coated solid support.

14. A method of reducing interference by free-hapten in an assay for detection of a target analyte in a patient sample, the method comprising:
  combining the patient sample, the hapten trap of claim 1, and at least two assay components for detection of a target analyte to form an assay solution, wherein at least one of the at least two assay components contains an analyte-specific binding partner, and wherein a first assay component comprises a hapten-assay conjugate and a second assay component comprises an anti-hapten specific binding partner (sbp); and
  performing an assay for detection of the target analyte on the assay solution by detecting assay signal generated by the at least two assay components.

15. The method of claim 14, wherein the hapten is biotin, the hapten-analog of the hapten trap is selected from the group consisting of 4'-hydroxyazobenzene-2-carboxylic acid (HABA) and 2-imino biotin, and the anti-hapten sbp of the hapten trap is selected from the group consisting of streptavidin, avidin, and traptavidin.

16. The method of claim 14, wherein the hapten is fluorescein, and the anti-hapten specific binding partner of the hapten trap is an anti-fluorescein antibody.

17. The method of claim 14, wherein the hapten conjugate of the first assay component is selected from the group consisting of a hapten-antibody conjugate, a hapten-antigen conjugate, a hapten-labeling enzyme conjugate, a hapten-analyte-under-test conjugate, a hapten-label conjugate, and a hapten-receptor conjugate.

18. The method of claim 14, wherein the hapten conjugate of the first assay component has a molecular weight of greater than about 1000 Daltons.

19. The method of claim 14, wherein the assay components comprise a biotinylated analyte-specific binding partner and a streptavidin coated solid support.

* * * * *